(12) United States Patent
Schon et al.

(10) Patent No.: US 6,241,522 B1
(45) Date of Patent: *Jun. 5, 2001

(54) GRINDING TOOL FOR DENTAL PURPOSES

(75) Inventors: Jurgen Schon, Kalletal; Michael Kullmer, Lemgo; Karl-Heinz Danger, Detmold, all of (DE)

(73) Assignee: Gebruder Brasseler GmbH & Co., Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/004,470

(22) Filed: Jan. 8, 1998

(30) Foreign Application Priority Data

Jan. 10, 1997 (DE) .................. 197 00 636

(51) Int. Cl.⁷ ........................................ A61C 3/06
(52) U.S. Cl. ........................... 433/166; 451/548
(58) Field of Search ................... 433/142, 165, 433/166; 451/541, 548, 549; 125/15

(56) References Cited

U.S. PATENT DOCUMENTS

| | | | |
|---|---|---|---|
| 927,164 | * 7/1909 | Puffer | 451/450 |
| 959,054 | * 5/1910 | Glover | 433/166 |
| 970,618 | * 9/1910 | Gardner | 451/548 |
| 1,700,634 | * 1/1929 | Hopf | 451/527 |
| 2,145,888 | * 2/1939 | Moulton et al. | 451/548 |
| 3,420,007 | * 1/1969 | Kolesh | 451/548 |
| 3,716,950 | * 2/1973 | McClure | 125/15 |
| 3,857,750 | * 12/1974 | Winter et al. | 51/298 |
| 4,350,497 | 9/1982 | Ogman | 51/296 |
| 4,661,064 | * 4/1987 | Beltramini | 433/166 |
| 4,718,398 | * 1/1988 | Hallez | 125/15 |
| 5,014,468 | * 5/1991 | Ravipati et al. | 51/295 |
| 5,020,283 | * 6/1991 | Tuttle | 451/550 |
| 5,083,922 | * 1/1992 | Yale | 433/166 |
| 5,125,838 | * 6/1992 | Seigneurin | 433/102 |
| 5,247,765 | * 9/1993 | Quintana | 51/209 R |
| 5,389,119 | * 2/1995 | Ferronato et al. | 51/296 |
| 5,470,273 | * 11/1995 | Mertens | 451/548 |
| 5,533,923 | * 7/1996 | Shamouilian et al. | 451/41 |
| 5,573,020 | * 11/1996 | Robinson | 132/322 |
| 5,674,122 | * 10/1997 | Krech | 451/536 |
| 5,782,682 | * 7/1998 | Han et al. | 451/548 |

FOREIGN PATENT DOCUMENTS 61-152375 * 7/1986 (JP) .......................... 125/15

* cited by examiner

Primary Examiner—John J. Wilson
(74) Attorney, Agent, or Firm—Sheppard, Mullin, Richter & Hampton LLP

(57) ABSTRACT

The present invention relates to a grinding tool for dental purposes comprising a support body which is covered at least in part with abrasive material, wherein at least a portion of the support body is provided with a honeycomb structure.

31 Claims, 5 Drawing Sheets

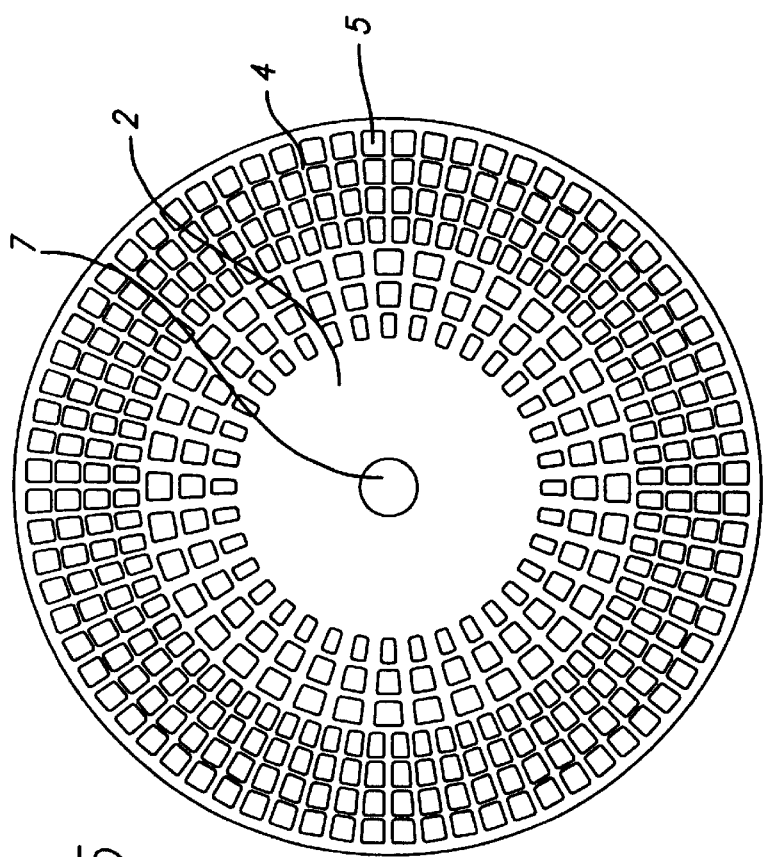
FIG. 5
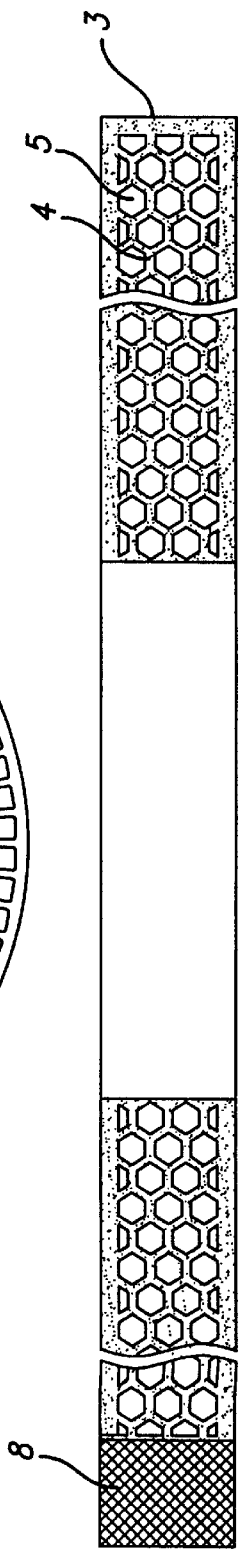
FIG. 10
FIG. 11

FIG. 6
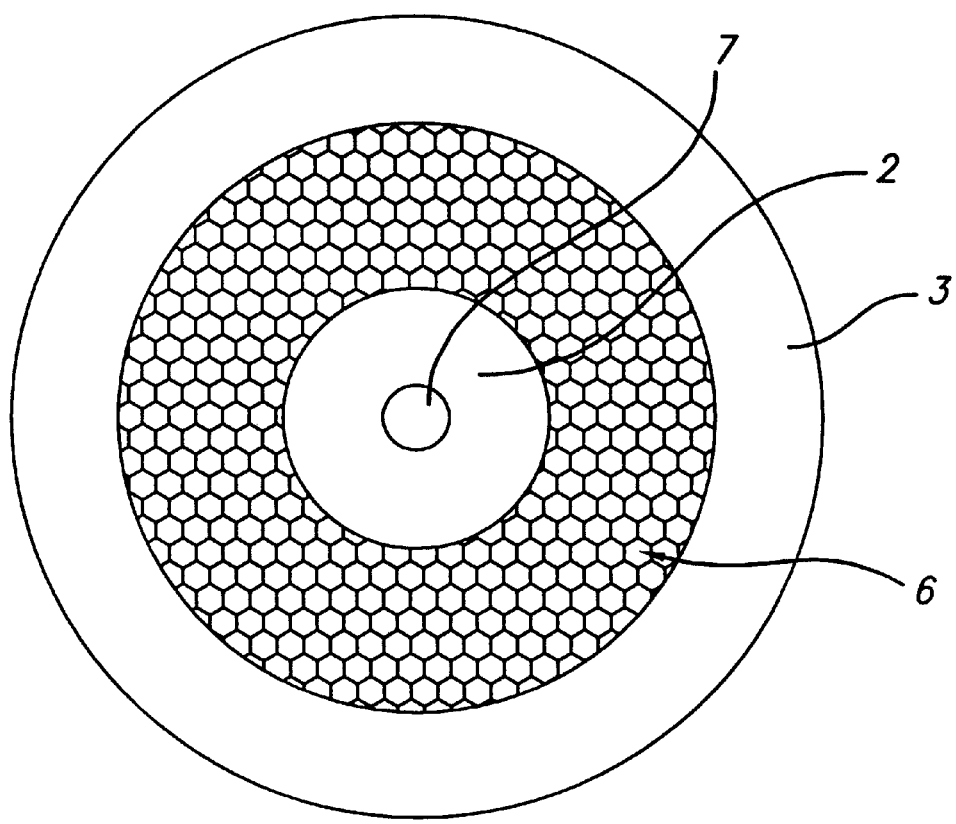
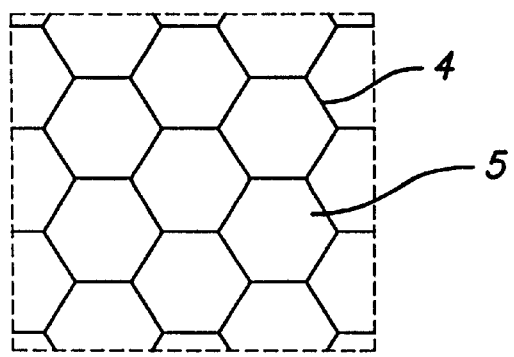
FIG. 7

GRINDING TOOL FOR DENTAL PURPOSES

This claims priority from German Application No. 197000636.1-23, filed Jan. 10, 1997.

BACKGROUND OF THE INVENTION

The present invention generally relates to a grinding tool for dental purposes.

In the dental field, for instance when teeth or dentures are prepared, many operations must be carried out with a grinding tool. Such grinding tools, which are preferably covered with diamond particles, are already known in the art. In general, dental grinding tools must be very thin so as to carry out extremely thin cuts, they must be flexible to treat curved, three-dimensional surfaces, and they must have an adequate degree of stability.

The rotating grinding tools of the invention can be used in dental laboratories. The strip-like grinding tools are usable in a dentist's office or in a dental laboratory. In general, two different types of grinding tool designs are known in the art. One type consists of a rotating tool which is shaped in the form of a circular disk that has a shaft, while the other type makes use of strips which are covered with abrasive particles.

Furthermore, it is therefore desirable to provide the grinding disk with recesses so that a dental technician or a dentist can look through the rotating disk and at the surface to be treated. These recesses are formed as relatively large holes which are arranged in the central portion.

SUMMARY OF THE INVENTION

It is the object of the present invention to provide a grinding tool of the above-mentioned type which can be easily produced and reliably used and which offers a high degree of flexibility and enables a user to look at the surface to be treated.

According to the invention this object is achieved in that the support body is provided with a honeycomb structure at least on portions thereof.

The grinding tool of the invention has a number of considerable advantages. With the honeycomb structure it is possible, on the one hand, to provide a plurality of recesses through which a viewer can look during rotation of the grinding disk. On the other hand, the honeycomb structure ensures an adequate degree of stability and strength, so that unintended movement, or the like, is not possible. Furthermore, the honeycomb structure ensures a maximum amount of flexibility, in particular in the area which is covered with the abrasive material. Hence, the grinding tool of the invention can also be used for treating strongly curved surfaces without the support body being permanently deformed.

Another advantage follows from the fact that additional machining space is formed by the honeycomb structure.

In an advantageous development of the present invention, the honeycomb structure comprises recesses defined by webs. These recesses may be shaped as hexagons or substantially as rectangles. It is possible to arrange the recesses in the form of a uniform pattern, but they may also be arranged as partial segments of a circle or a circular disk. This is especially advantageous in the case of substantially rectangular recesses.

Furthermore, it is advantageous according to the invention when the webs are covered with abrasive material, for instance with diamond particles. The abrasive material is applied in the same manner as is known from the prior art, so that a detailed description can be dispensed with.

The web structure of the invention may be designed such that it comprises embossments defined by webs. These embossments are shaped in the form of beads and increase the stability of the support body.

The size of the individual webs can be adapted to the respective requirements; it is possible to use very fine honeycombs or large-sized honeycombs. Furthermore, different concentric portions of the support body can be provided with differently designed honeycomb structures. It is also possible to arrange the honeycomb structure just on a few concentric portions, or the honeycomb structure may only be provided on segment-like portions. However, it goes without saying that the support body according to the invention may also be provided with the honeycomb structure substantially over the whole surface.

Furthermore, it is advantageous to arrange a combination of web structures with recesses or embossments. For instance, the strength of the support body can be increased by just providing embossments in the central or middle portion, while the recesses are arranged on an edge portion.

According to the invention the support body can be made from a metallic material or a plastic material. When a metallic material is used, spring band steel, titanium, a titanium-nickel alloy, or the like, may be used.

In sum, the present invention relates to a grinding tool for dental purposes comprising a support body which is covered at least in part with abrasive material, characterized in that the support body is provided with a honeycomb structure, at least on portions thereof.

Other features and advantages of the present invention will become apparent from the following description of the preferred embodiments, taken in conjunction with the accompanying drawings, which illustrate, by way of example, the principles of the invention.

BRIEF DESCRIPTION OF THE DRAWINGS

The following drawings illustrate the preferred embodiments of the invention. In such drawings:

FIG. 5 is a top view of a third embodiment according to the present invention;

FIG. 6 is a top view of a fourth embodiment having a honeycomb structure with embossments;

FIG. 7 is a partial view of the web structure shown in FIG. 6;

FIG. 10 is a top view of a seventh embodiment that is a grinding strip formed in accordance with the invention; and FIG. 11 is a side view of the strip shown in FIG. 10.

DESCRIPTION OF THE PREFERRED EMBODIMENTS

The grinding tool of the invention shown in FIGS. 1–9 comprises a shaft 1 which, as is known from the prior art, can be clamped into a drive means. The free end of shaft 1 has secured thereto a substantially circular disk-shaped support body 2 whose edge portion, which is shaped in the form of a concentric ring, is covered with an abrasive material 3. The cover is provided at both sides in order to treat surfaces or to make cuts.

Figure 1:
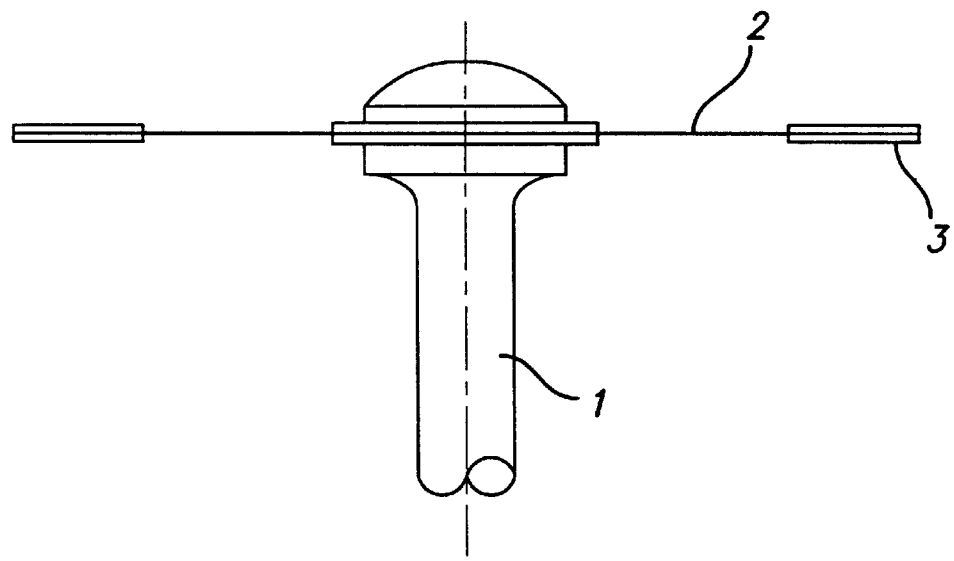
FIG. 1 is a diagrammatic side view, in partial section, of an embodiment of a grinding tool according to the invention.
Figure 2:
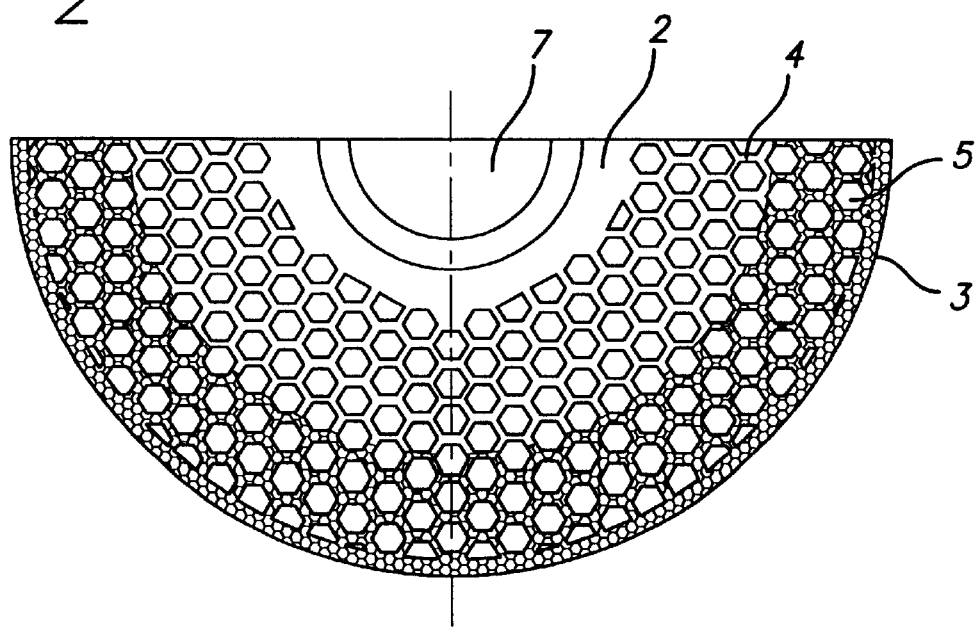
FIG. 2 is a partial top view on the tool shown in FIG. 1.

FIG. 2 is a top view of the dental grinding tool shown in FIG. 1. A recess 7 (FIG. 3) which serves fastening purposes with respect to shaft 1 is formed in the center. Next to the central portion, the support body 2 has a honeycomb structure which comprises a uniform arrangement of hexagons and is thus formed by webs 4 and recesses 5.

As already explained with reference to FIG. 1, a concentric edge portion is covered at both sides with the abrasive material 3, the latter being thus applied to webs 4. The abrasive material which preferably contains diamond grains or diamond particles is applied in the manner known from the prior art, for instance in an electrolytic process.

The embodiment shown in FIGS. 1 and 2 offers maximum stability and flexibility while the great number of recesses 5 ensures an unobstructed view through the rotating grinding tool.

The honeycomb-like configuration of support body 2 is comparable to a shear blade of an electric shaver; the support body 2 is preferably made from spring steel. The support body may, for instance, have a thickness of from 0.02 mm to 0.04 mm, resulting, for instance, in an overall thickness of from 0.1 mm to 0.15 mm, including the applied coating of abrasive material.

Figure 3:
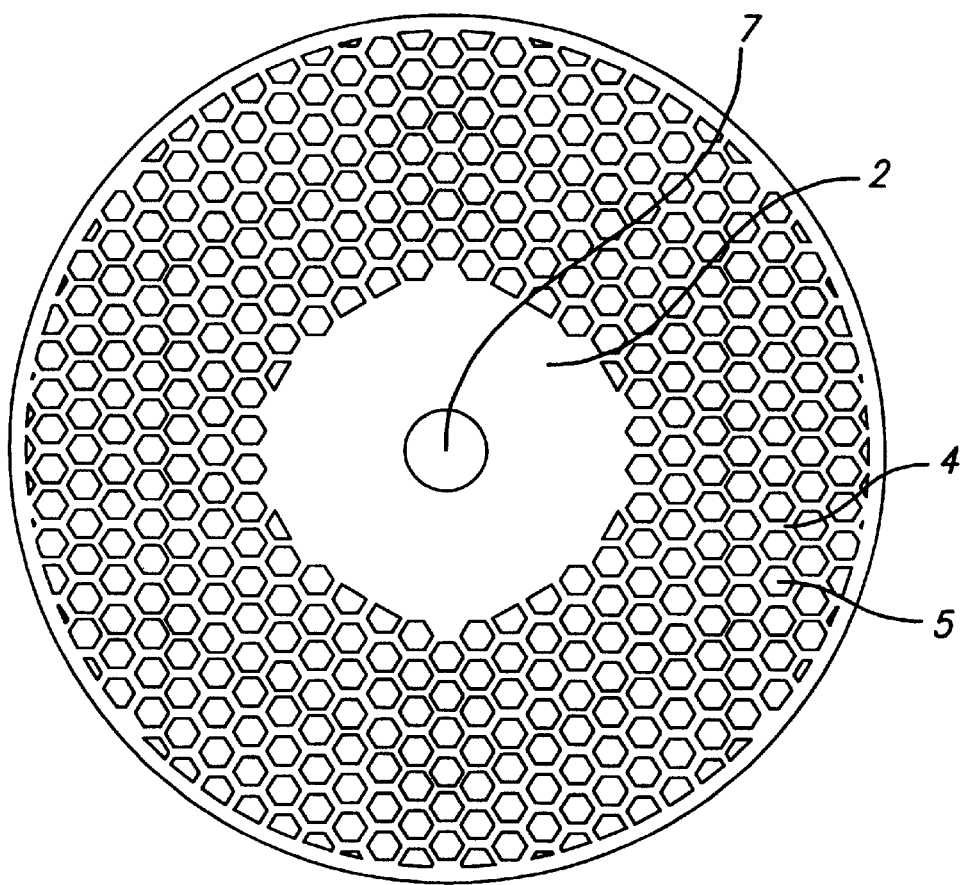
FIG. 3 is a top view of a second embodiment of a grinding tool according to the invention.
Figure 4:
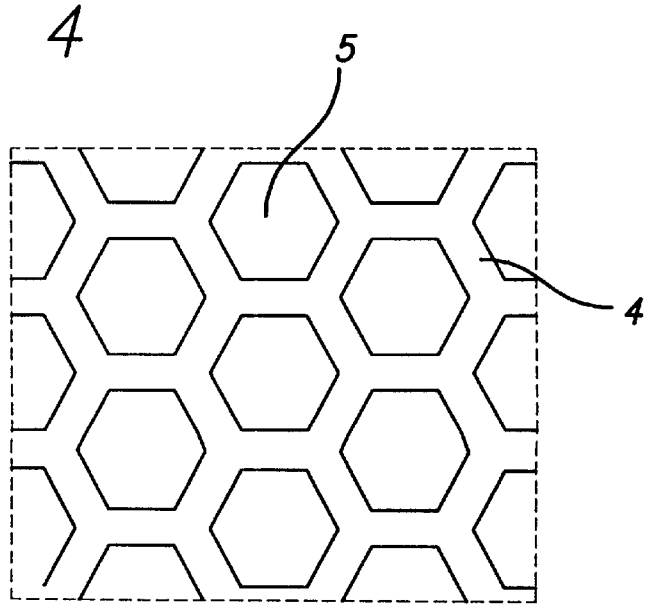
FIG. 4 is an enlarged view of a detail of the honeycomb structure shown in FIG. 3.

FIGS. 3 and 4 show a further variant in which the honeycomb structure, in particular, can be seen in a very clear manner. The grinding tool is covered with abrasive material over the whole surface.

FIG. 5 shows a modified embodiment in which the honeycomb structure comprises rectangles which are radially arranged and thus form a uniform pattern with webs of a uniform width. It is here also possible to vary the stability and visibility of the grinding disk by changing the size and arrangement of the individual recesses.

FIGS. 6 and 7 show a further embodiment in which the concentric edge range which is covered with the abrasive material 3 is formed without any honeycombs, while the honeycomb structure is just found in the concentric center portion. The web structure has bead-like embossments 6 which are defined by webs 4 (see FIG. 7). Hence, in this embodiment, it is not possible to look through the grinding disk; rather, the embossments 6 of the honeycomb structure improve the total stability.

Figure 8:
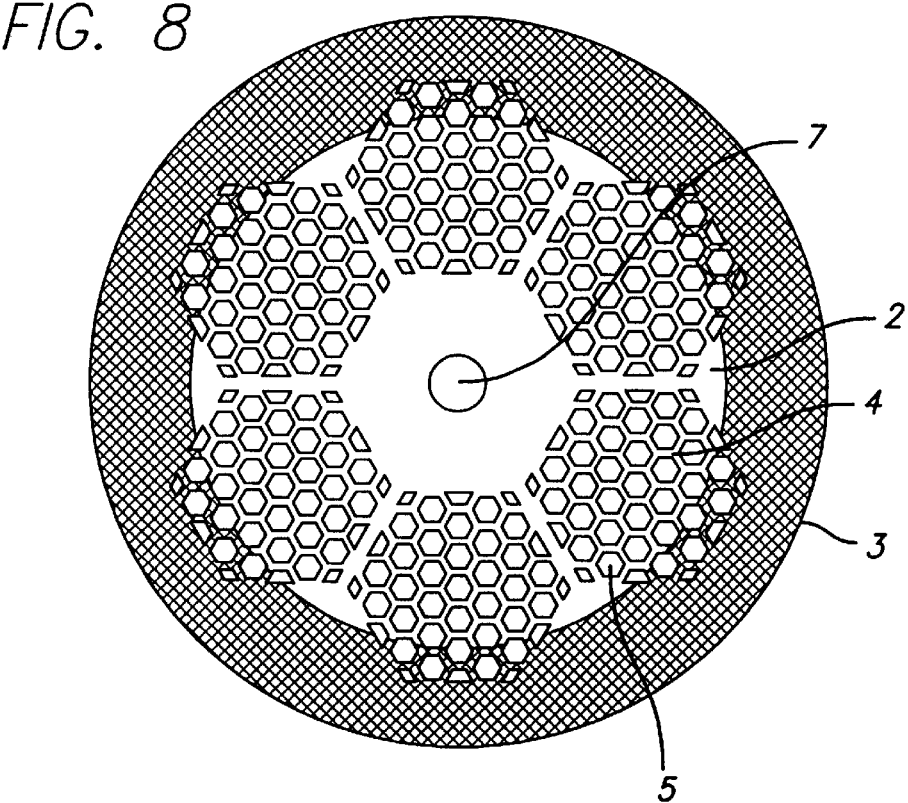
FIG. 8 is a top view of a fifth embodiment of a grinding disk according to the invention.

FIG. 8 shows a further embodiment of a grinding disk of the invention, in which an outer concentric edge portion is covered with the abrasive material 3. The honeycombs of the honeycomb structure are radially formed on the inside next to the outer edge portion and comprise defined hexagonal recesses 5 as in the preceding embodiments of webs 4. The web structure is arranged in the form of six corners. This yields maximum stability, together with the possibility of having an unobstructed view through the rotating tool.

Figure 9:
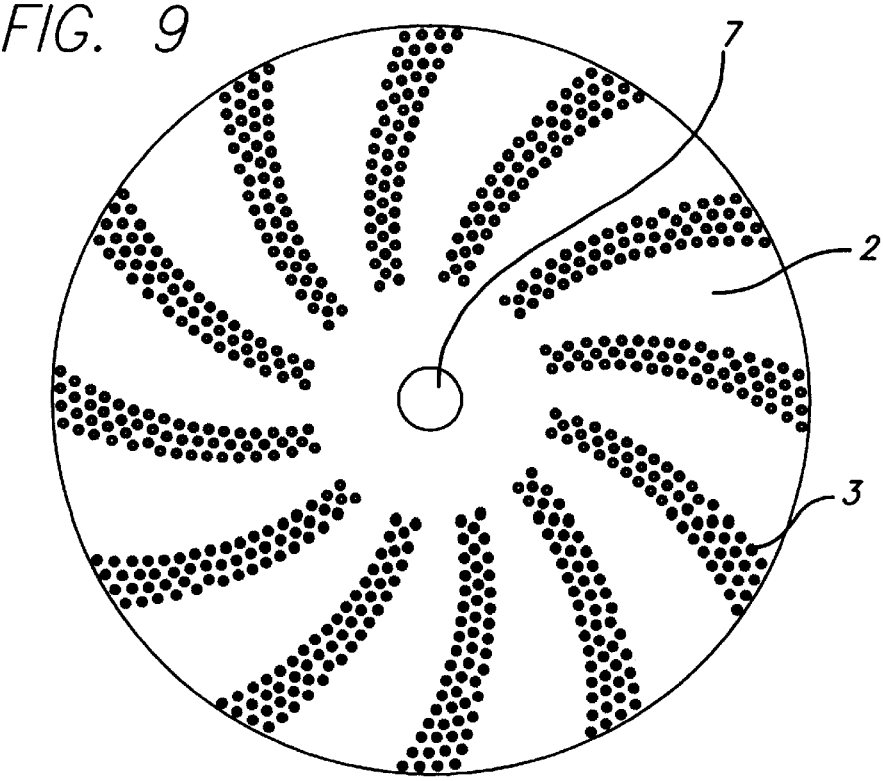
FIG. 9 is a top view of a sixth embodiment of a grinding disk.

FIG. 9 shows a further variant in which the honeycomb structures are applied in the form of an arc or tail. The abrasive material may either be applied in the area of the honeycomb structure or in the area of the spaces.

FIGS. 10 and 11 show an entirely different embodiment of the grinding tool of the invention. This tool is shaped like a strip and is provided on its respective edge portion with a web structure which comprises hexagonal recesses 5 which are also defined by webs 4. The webs and the remaining edge portions are covered with the abrasive material 3. The center portion of the strip is neither provided with a honeycomb structure nor equipped with a honeycomb structure. The edge portion which is shown at the left side in FIG. 10 comprises an identification field 8, for instance, in order to apply a color marking, or the like.

Many modifications and variations are thus possible within the scope of the present invention with respect to the strips, the dimensions thereof and also with respect to the size of the rotating grinding disks. The grinding tools of the invention can thus be adapted in a very easy manner to satisfy different requirements.

The present invention is not limited to the illustrated embodiments; rather many variations and modifications are possible within the scope of the present invention.

We claim:

1. A dental grinding tool comprising:
   a support body which is covered at least in part with abrasive material, wherein at least a portion of the support body is provided with a honeycomb structure; and
   wherein the honeycomb structure comprises hexagonal recesses defined by webs, the recesses extending through the support body to define holes therethrough.

2. The dental grinding tool according to claim 1, wherein the webs are covered with abrasive material.

3. The dental grinding tool according to claim 1, wherein the honeycomb structure is formed on concentric portions of a circular disk-shaped support body.

4. The dental grinding tool according to claim 1, wherein the honeycomb structure is formed on segment-like portions of the support body.

5. The dental grinding tool according to claim 1, wherein the support body is substantially provided over the whole surface with the honeycomb structure.

6. The dental grinding tool according to claim 1, wherein the support body is provided in a concentric center portion with the honeycomb structure.

7. The dental grinding tool according to claim 1, wherein the honeycomb structure comprises recesses and embossments.

8. The dental grinding tool according to claim 7, wherein different concentric portions are provided with recesses or embossments.

9. The dental grinding tool according to claim 1, wherein the honeycomb structure has a uniform shape.

10. The dental grinding tool according to claim 1, wherein the support body is made from a metallic material.

11. The dental grinding tool according to claim 10, wherein the support body is made from spring steel.

12. The dental grinding tool according to claim 10, wherein the support body is made from titanium material.

13. The dental grinding tool according to claim 10, wherein the support body is made from nickel-titanium alloy.

14. The dental grinding tool according to claim 1, wherein the support body is made from plastic material.

15. The dental grinding tool according to claim 1, wherein the abrasive material comprises diamond particles.

16. A dental grinding tool comprising:
   a support body which is covered at least in part with abrasive material, wherein at least a portion of the support body is provided with a honeycomb structure;
   wherein the honeycomb structure comprises recesses defined by webs, the recesses extending through the support body to define holes therethrough; and, wherein the recesses are substantially shaped in the form of rectangles, said rectangles being shaped as partial segments of a circle or a circular disk.

17. A dental grinding tool comprising:

a support body which is covered at least in part with abrasive material, wherein at least a portion of the support body is provided with a honeycomb structure;

wherein the honeycomb structure comprises recesses defined by webs, the recesses extending through the support body to define holes therethrough; and wherein the honeycomb structure comprises hexagonal embossments defined by webs.

18. A dental grinding tool comprising:

a support body which is covered at least in part with abrasive material, wherein at least a portion of the support body is provided with a honeycomb structure;

wherein the honeycomb structure comprises recesses defined by webs, the recesses extending through the support body to define holes therethrough; and wherein the honeycomb structure comprises rectangular embossments defined by webs, said rectangles being shaped as partial segments of a circle or a circular disk.

19. A dental grinding tool comprising:

a disk-shaped support body which is covered at least in part with abrasive material, wherein at least a portion of the support body is provided with a honeycomb structure; and wherein the honeycomb structure is located on a plurality of separate curved portions on the disk-shaped support body, each curved portion arcing radially outwardly on the support body.

20. The dental grinding tool according to claim 19, wherein the honeycomb structure defines a plurality of recesses, at least one recess extending through the support body to define holes therethrough.

21. The dental grinding tool according to claim 20, wherein the honeycomb structure is coated with abrasive material.

22. The dental grinding tool according to claim 20, wherein the surface of the support body between the honeycomb structures is coated with abrasive material.

23. The dental grinding tool according to claim 19, wherein the honeycomb structure is coated with abrasive material.

24. The dental grinding tool according to claim 19, wherein the surface of the support body between the honeycomb structures is coated with abrasive material.

25. The dental grinding tool according to claim 19, wherein the support body is disk-shaped and wherein the honeycomb structure is coated with abrasive material.

26. The dental grinding tool according to claim 19, wherein the support body is disk-shaped and wherein the surface of the support body between the honeycomb structures is coated with abrasive material.

27. A dental grinding tool comprising:

a support body covered at least in part with abrasive material, wherein at least a portion of the support body is provided with a web structure; and wherein the web structure defines a plurality of recesses, the recesses extending through the support body to define holes therethrough; and wherein the web structure is located on a plurality of separate curved portions on the circular disk-shaped support body, each curved portion arcing away from the center of the disc-shaped support body.

28. The dental grinding tool according to claim 27, wherein the recesses are shaped in the form of hexagons.

29. The dental grinding tool according to claim 27, wherein the recesses are substantially shaped in the form of rectangles.

30. The dental grinding tool according to claim 29, wherein the rectangles are shaped as partial segments of a circle or a circular disk.

31. The dental grinding tool according to claim 27, wherein the webs are covered with abrasive material.

* * * * *